United States Patent [19]
Fiz

[11] Patent Number: 5,951,558
[45] Date of Patent: Sep. 14, 1999

[54] BONE FIXATION DEVICE

[76] Inventor: Daniel Fiz, 754, 9th Floor "B", Buenos Aires, Argentina

[21] Appl. No.: 09/154,997

[22] Filed: Sep. 17, 1998

[30] Foreign Application Priority Data

Apr. 22, 1998 [AR] Argentina ................. P980101860

[51] Int. Cl.⁶ .................................................. A61B 17/80
[52] U.S. Cl. ............................................. 606/70; 606/69
[58] Field of Search ................... 606/69, 70, 71, 606/72, 73, 61, 60

[56] References Cited

U.S. PATENT DOCUMENTS

| | | | |
|---|---|---|---|
| 5,190,544 | 3/1993 | Chapman et al. | 606/69 |
| 5,330,477 | 7/1994 | Crook | 606/69 |
| 5,364,399 | 11/1994 | Lowery | 606/69 |
| 5,665,089 | 9/1997 | Dall et al. | 606/70 |
| 5,810,824 | 9/1998 | Chan | 606/70 |

*Primary Examiner*—Guy V. Tucker
*Attorney, Agent, or Firm*—Darby & Darby

[57] ABSTRACT

Bone fixation device for keeping two or more bone pieces together, either pieces of a broken bone or two distinct bones, for undergoing junction of the pieces by natural welding, the device being capable of immobilizing flat or round bones, long or short bones, parts of a broken femur or two contiguous vertebrae, the device comprising a fixation plate and fixation screws, the plate having orifices for passing the screws through the plate and fastening the screws into the bone tissue, a screw blocking or locking mechanism being provided in the plate to block the screws in the fastening position once the screws have been passed through the plate and screwed into the bone pieces, for preventing the screws from unscrewing from the bone pieces and moving out of the fixation plate once and after the fixation plate and the screws have been firmly installed in the bones, with the risk of entering into contact with the patient inner tissues, muscles or organs, the blocking mechanism being easily operated by a surgeon or a surgeon assistance.

12 Claims, 2 Drawing Sheets

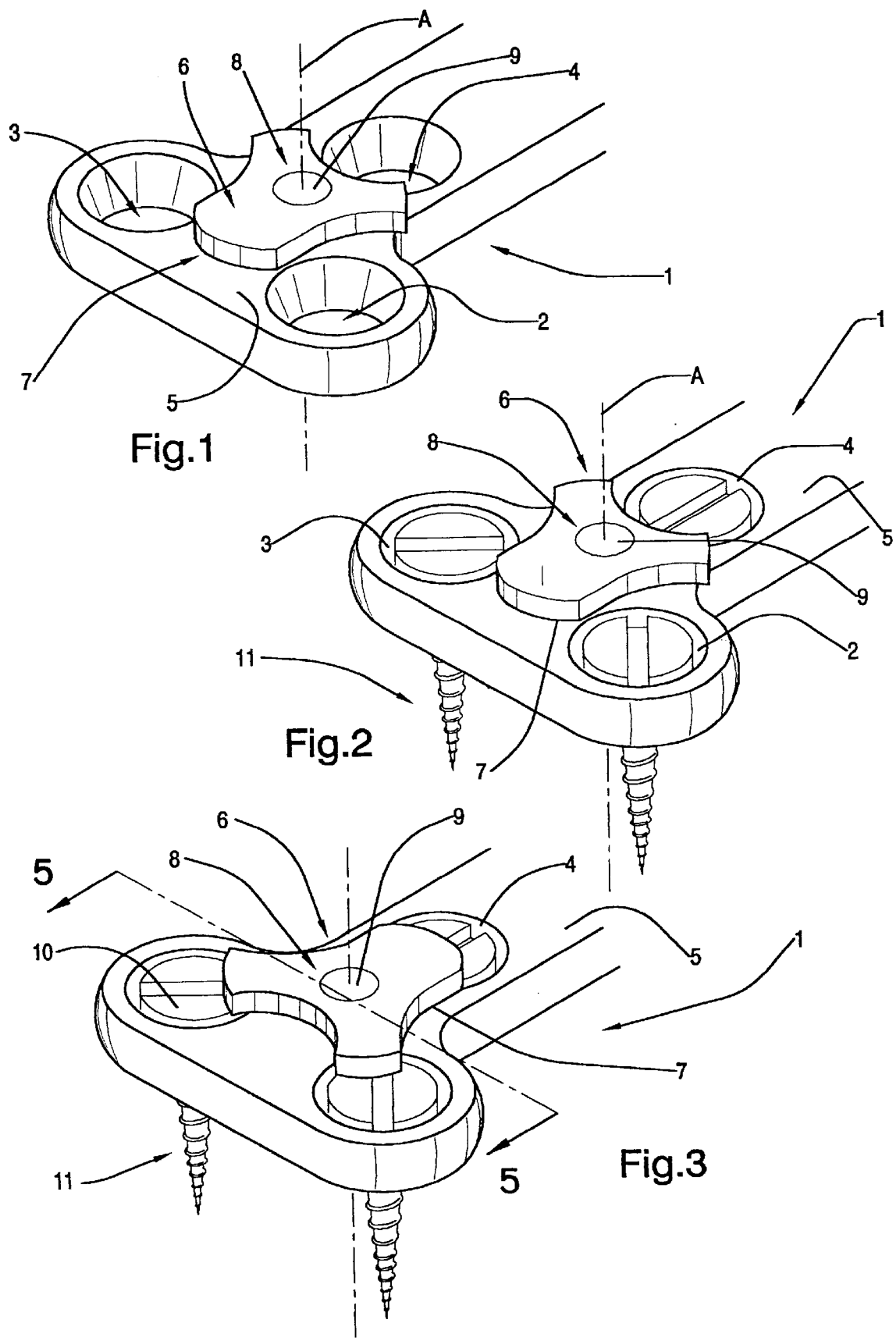

BONE FIXATION DEVICE

BACKGROUND OF THE INVENTION

1. Field of the Invention

The present invention relates to a bone fixation device for immobilizing two or more bone pieces and keeping them firmly together whereby the pieces are immobilized at least for a period of time they need to undergo a natural welding, and more particularly the invention relates to blocking means for securing fastening means used in the device.

To the purpose of the present specification the term "bone piece" is meant any bone or bone piece resulting from the breaking of one or more bones, which pieces must be firmly immobilized together, for example to undergo natural welding, and the bone pieces, bones, or parts of these bones may be flat, long, short, or round bodies.

2. Description of the Prior Art

It is well known to use fixation plates to keep two or more bones or bone pieces together to promote natural and accurate welding of the bones. These plates are located against the bones to be welded and firmly fixed to the bone parts by fixation screws that are passed through fixation orifices generally located at the ends of the plates, and screwed in the bones. Thus, the plate remains firmly fixed to the bone parts to be joined and the parts are kept firm together in contact enough to facilitate correct welding of the bones. After some time, however, due to the movements of the patient, the screws may become loosen and may move out of the plate orifices with the serious consequences this would involve against the patient tissues, muscles or organs close to the plate.

Some approaches have been made to avoid as much as possible the loosing of the fastening screws to prevent the patient from being subject to the above mentioned consequences. A known technique consists of distorting or deforming a head of the fixation screw once the screw is entirely installed in the fixation plate and firmly screwed in bone. That is, once the screw has being passed through the plate orifice and secured into the bone tissue the head of the screw is distorted or deformed by punching or hammering the same within the plate orifice. The head deformation would prevent the head from moving relative to the orifice, whereby loosening of the screw is minimized. The technique, however, is very traumatic to the patient and risky to the integrity of the bone or bone pieces under treatment which are exposed to the important impacts from the hammering or punching operation.

Other fixation plates include an additional threaded bore parallel and adjacent the corresponding plate fixation orifice. A small locking screw is threaded in such bore, the small screw having a head and a threaded stem or shaft eccentrically pending from the head. The small locking screw is screwed without reaching the total screwing capacity of the screw and with a largest portion of the head, that is the portion more eccentrically extended relative to the stem, located away from contact with the head of the associated fixation screw. When the fixation screw has been firmly screwed in the bone, the locking screw is additionally screwed until the more eccentrically extended head portion abuts the head of the fixation screw and enters into an intimate and forced contact with the fixation screw to lock and retain the same in place by pressure against its head.

A fixation plate using locking means similar to the above disclosed also has an additional bore, adjacent and parallel to the fixation bore and an additional small locking screw with a head including a cut portion or straight sector. The cut portion of the screw head is located in such a way that the fixation orifice is not obstructed by this head and is free to receive the fixation screw therethrough. Once the fixation screw has been firmly fixed into the bone, the locking screw is rotated, by screwing the same in the fixation plate, so as the head of the locking screw out of the cut portion makes and intimate and forced contact against the periphery of the head of the fixation screw and lock and retain the same in position. In the two above embodiments provided in the prior art the same drawbacks remain without a solution being provided. That is, the problem of loosing the fixation screw seems to be solved by locking the fixation screw with an additional locking small screw which is now subject to the same loosing situation as it was with the fixation screw. In addition, there are many parts provided in the fixation plate, that is, the number of screws is duplicated as long as a new locking screw is necessary for locking each fixation screw, making the fixation plate more complex to be operated and highly risky for the patient.

Another fixation plate also known in the art consists of a plate including a flat disc with a central opening. Once the fixation screws have been screwed in position and the bone parts are firmly retained by the plate, the disc is located over the screw orifices, covering the fixation screw heads, and an additional screw is passed through the central opening of the disc and fixed against the plate by screwing the additional screw into the bone tissue. Again, while the number of additional locking means are reduced as compared to the above described fixation plates, this locking plate requires an additional screw which is not locked by any additional means to prevent this screw from loosening, with the enormous risk of having the disc released from the plate resulting in a dangerous potential situation for the patient.

Concluding, according to the prior art, all the fixation plates have been developed by approaching the problem of loosening fixation screws through the provision of additional screws in an attempt to lock the fixation screws in position and prevent the involuntary unscrewing thereof. Many additional elements are in this way involved in the approaches of the prior art, these many members not only increasing the risks for the patient but also increasing the work and time involved in installing of the plates and fixing of the same onto the bones.

It would be therefore very desirable and convenient to count on a new fixation plate capable of preventing the loosening of the fixation screws without using additional locking screws ore separate pieces subject to accidental releasing from the plate, within the patient's body, the new device being capable of being operated without involving too much time and work, as well as without complex operations being necessary.

SUMMARY OF THE INVENTION

It is therefore one object of the present invention to provide a bone fixation device for keeping two or more bone pieces together, either pieces of a broken bone or two distinct bones, for undergoing junction of the pieces by natural welding, the device being capable of immobilizing flat or round bones, long or short bones, parts of a broken femur or two contiguous vertebrae, the device comprising a fixation plate and fixation screws, the plate having orifices for passing the screws through the plate and fastening the screws into the bone tissue, screw blocking or locking means being provided in the plate to block the screws in the fastening position once the screws have been passed through the plate and screwed into the bone pieces, for preventing the screws from unscrewing from the bone pieces and moving out of the fixation plate once and after the fixation plate and the screws have been firmly installed in the bones, with the risk of entering into contact with the patient inner tissues, muscles or organs, the blocking means being easily operated by a surgeon or a surgeon assistance.

It is still another object of the present invention to provide a bone fixation device for fixing together at least two bone pieces for undergoing junction by natural welding, the device comprising a fixation plate having orifices for passing screws through the plate; a screw passing through each orifice of the plate for fixing the plate to the bone pieces which are to be joined together; screw blocking or locking means in the plate for blocking the screws in position once the screws have been passed through the plate and screwed into the bone pieces, and for preventing the screws from unscrewing from the bone pieces, the blocking means being movably, either slidably or rotatably, mounted in the fixation plate and arranged close to the orifices to move between an unlocking position where the orifices are unobstructed to receive the screws, and a blocking position to close at least partially the orifices once the screws have been passed through the orifices and screwed in the bones, so as to prevent the screws located in the corresponding orifices from loosing and releasing from the orifices.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 1 shows a top perspective view of an end portion of a fixation device according to the invention, the device portion including three fixation orifices, for receiving the fixation screws (not shown in this Figure) and the inventive locking/blocking means;

FIG. 2 shows a top perspective view similar to FIG. 1, with three fixation screws in the corresponding fixation orifices and the blocking means in the unlocking position;

FIG. 3 shows a top perspective view similar to FIG. 2, with the blocking means rotated to the blocking position;

DESCRIPTION OF THE PREFERRED EMBODIMENTS

Figure 4:
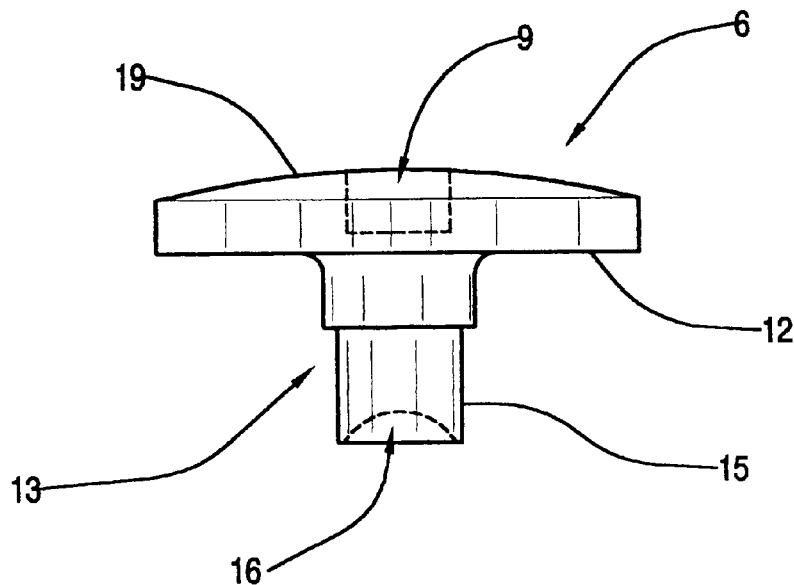
FIG. 4 shows a side elevation view of the blocking rotary plate.

Now referring in detail to the drawings it may be seen from FIG. 1–3 a fixation plate 1 including three fixation orifices 2–4 and blocking means 6 according to the invention. While only an end portion of plate 1 is illustrated in FIGS. 1–3, plate 1 comprises an elongated body with an opposite end portion identical to the depicted portion. That is, one end portion will be fixed to one of the bone pieces to be immobilized together, while the opposite end portion is to be fixed to the other bone piece. For clarity purposes, only one end portion has been illustrated in the drawings. The fixation plate, however, may have any convenient shape, depending on the bone pieces to be joined, thus, the plate my be square, rectangular, circular or star-like configured.

Figure 5:
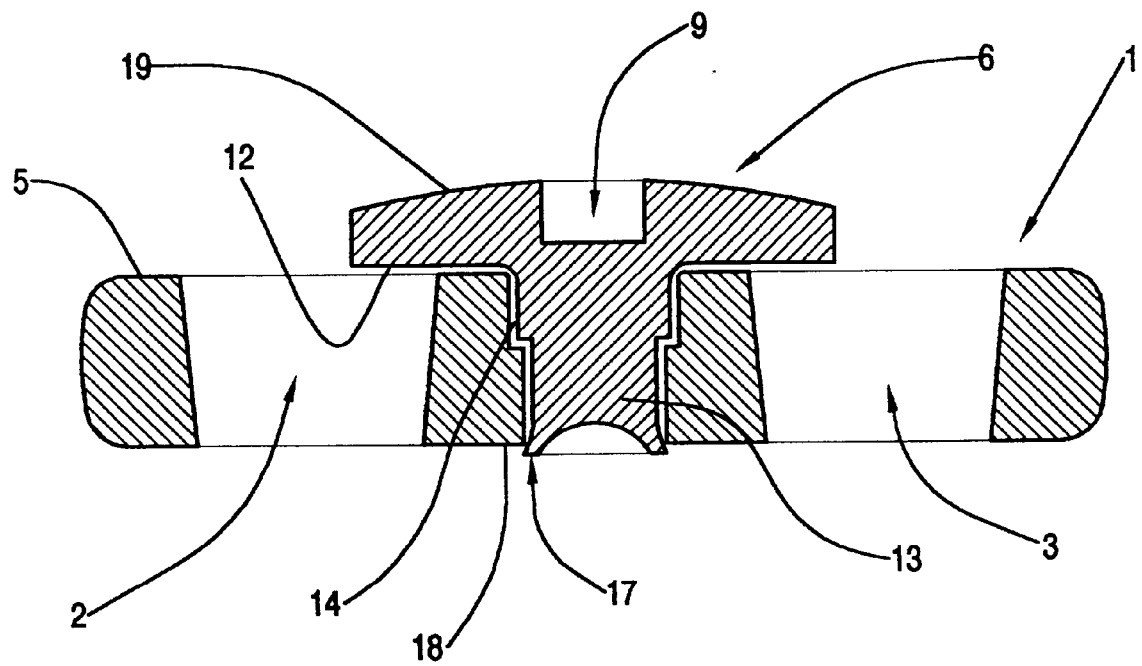
FIG. 5 shows a cross-section view taken along line V—V of FIG. 3.

On an upper face 7 of plate 1 the invented blocking means devised by a rotary blocking plate 6 to which detailed reference will be made later in relation to FIGS. 4, 5. Within each orifice 2–4 a corresponding fixation screw, all the screws being indicated by numeral reference 11 and having screw heads 10, is inserted and passed through the corresponding orifice to be then screwed into the bone (not shown), whereby the plate is firmly fixed to the associated bone or bone part to be joined together for subsequent natural welding.

Upon entirely screwing of the screws 11 in the bone, screw heads 10 remains within orifices 2–4, and abuts against an inner surface of the corresponding orifice to retain the plate against the bone. The inner surface of the fixation orifices may be conical, as shown in FIG. 5. Head 10, in addition, remains below the level of an upper face 5 or at the same level of face 5 of the plate, that is leveled with face 5. Like in the plates of the prior art, screws 10 are subject to the mechanical action of impacts and movements of the patient while the bones are naturally welding to each other. As a result of this movement the screws may become loose and release from the bone. To prevent the screws for loosening, the present invention provides blocking plate 6 which is rotatably mounted on plate 1, against upper face 5. In other words, the screw blocking means retains screws 11 in position once the screws have been passed through the plate and screwed into the bone pieces, and prevents the screws from unscrewing from the bone pieces.

Blocking plate 6 is rotatably mounted around axis "A", at a central rotation portion 8 thereof, in the fixation plate and arranged close to orifices 2–4, preferably in a virtual center of the orifices arrangement, particularly when each orifice is located at a corresponding vertex of a virtual triangle. Thus, blocking plate 6 will rotatably move between an unlocking position, shown in FIGS. 1, 2, where the orifices are unobstructed to receive the screws, and a blocking position, shown in FIG. 3, to close or obstruct, at least partially, orifices 2–4, once the screws have been passed through the orifices and screwed in the bones, so as to prevent the screws located in the corresponding orifices from loosing and releasing from the orifices.

To efficiently obstruct orifices 2–4 once the screws are inside the orifices, blocking plate 6 has three radially extended arms 7 each defining a blocking portion of the plate, capable of being located over a corresponding orifice 2–4 in the blocking position of the blocking plate. Arms 7 are arranged in the same configuration like orifices 2–4 and are radially extended from central rotation portion 8 of the blocking plate. More particularly, plate 6 has a star-like configuration with the three radially extended arms 7 being equally spaced apart from each other around the rotation central portion, forming 120° angles, so as to be in simultaneous coincidence with the orifices of the fixation plate when the plate is rotated to be placed in the blocking position shown in FIG. 3.

The periphery of plate 6, between arms 7, may have a smooth curved configuration so as to accommodate to orifices 2–4 without causing and obstruction of same when plate 6 is in the unlocking position.

Although orifices 2–4 are shown partially closed or obstructed by arms 7, the orifices may be entirely covered by the arms, but this alternative would not be necessary as long as with the partial overlapping the screws are unable to move out of the orifices even if the screws become loose from the bones. The terms "blocking" and "locking" are indistinctly used in relation to the means of the invention as far as screws 11 will be "blocked" and/or "locked" in position depending on whether head 10 remains below the level of upper face 5 or at the level of face 5. If head 10 is below the level of face 5, screw 11 may become loosen but it will be "blocked" within orifice 2–4, that is prevented from releasing from the bone. If head 10 is at the level of face 5, the head will be not only blocked but also locked in position because it will be in contact with a bottom face 12 of blocking/locking plate 6.

Blocking plate 6 is rotatably connected to the fixation plate through a rotation shaft 13 projecting from the blocking plate and rotatably connected to the fixation plate in a mounting bore 14 provided at the center of fixation plate 6. To be rotatably freely retained into bore 14 and prevented, however, from any axial movement, rotation shaft 13 has a bottom end with a recess 16 provided to facilitate, after the insertion of shaft 13 into bore 14, a riveting operation of an end 15 to form a riveted portion 17 overlapping against a bottom face 18 of plate 1.

Riveting of shaft 13 against plate 1 is carried out with the purpose of providing some interference between upper face 5 of plate 1 and bottom face 12 of plate 6 so as to put both faces in intimate contact, and create a high friction between faces 5, 12, whereby the relative position between the plates are safely kept and any relative movement, particularly when the blocking is in the blocking position, is prevented. The friction between faces 5, 12 may be increased, if desired, by providing one or both faces with surface textures.

On a top face 19 blocking plate 6 is provided with manually actuated means for rotating the plate and placing the same in the desired position, for example, in the blocking position. The manually actuated means may comprise a recess 9 for receiving some kind of actuating tools, such as a screwdriver. Recess 9 are illustrated in coincidence with rotation axis "A" but two or more recesses may be provided out of coincidence with axis "A". Blocking plate 6 may also be rotated by taken the same from its arms 7.

Fixation plate 1 is provided with external faces and surfaces flat and smooth enough to avoid any discomfort for the patient. Particularly, top face 19 of blocking plate 6 is provided with a smoothly curved design, including no-sharp edges.

The fixation plate and said blocking plate, as well as all the intervening elements, are made of a bio-compatible material, such as platinum or any other biological metal.

While preferred embodiments of the present invention have been illustrated and described, it will be obvious to those skilled in the art that various changes and modifications may be made therein without departing from the scope of the invention as defined in the appended claims. For example, the quantity of fixation orifices and corresponding blocking arms will depend on the type of bones, size and form thereof. Orifices 2–4 may have a cylindrical conical shape, as shown in FIG. 5, however, the same may be cylindrical with a bottom flange or rim on which the head of the screw abuts to firmly retain the fixation plate against the bones.

I claim:

1. A bone fixation device for fixing together at least two bone pieces for undergoing junction by natural welding, the device comprising:

a fixation plate having orifices each for passing a screw through the plate for fixing the plate to the bone pieces by screwing into the bone tissue; and a screw blocking plate rotatably mounted to said fixation plate by a shaft and rotatable between an unlocking position where the orifices are unobstructed to receive the screws, and a blocking position to at least partially cover the orifices and screws therein to prevent the screws from loosening and releasing from the orifices.

2. The bone fixation device of claim 1, wherein said blocking plate has blocking portions to be simultaneously located over said orifices in the blocking position of said blocking plate to overlie all of said orifices.

3. The bone fixation device of claim 2, wherein said blocking plate shaft projects from said blocking plate and is rotatably inserted into a mounting bore of said fixation plate.

4. The bone fixation device of claim 2, wherein said rotation shaft has a distal end riveted against a bottom face of said fixation plate to retain said rotation shaft to said fixation plate while leaving said blocking plate free to rotate within the bore.

5. The bone fixation device of claim 2, wherein said blocking portions comprise arms radially extended from a central rotation portion of said blocking plate.

6. The bone fixation device of claim 5, wherein said fixation plate has three orifices for the screws, the orifices being equally spaced around said rotation bore, said blocking plate having a star configuration with three radially extended arms defining three blocking portions, the arms being equally spaced apart from each other around said blocking plate central portion, forming 120° angles, so as to be in simultaneous coincidence with the three orifices of said fixation plate in the blocking position of said blocking plate.

7. The bone fixation device of claim 2, wherein said fixation plate and said blocking plate are made of a bio-compatible material.

8. The bone fixation device of claim 2, wherein said blocking plate has a bottom flat face engaging against an upper flat face of said fixation plate, both faces being in intimate contact with high friction therebetween to maintain the relative positions between said plates.

9. The bone fixation device of claim 2, wherein said blocking plate has means to accept a device to manually rotate said blocking plate to the blocking position.

10. The bone fixation device of claim 1, wherein at the blocking position, the orifices of said fixation plate are partially obstructed by said blocking portions of said blocking plate.

11. The bone fixation device of claim 1, wherein said orifices are circular cylindrical orifices and further comprising a screw that has a head acting against a wall of a said orifice with the head of the screw, when affixed to the bone, remaining within the orifice below or flush with the upper face of said fixation plate.

12. The bone fixation device of claim 11, wherein said orifices are conical.

* * * * *

UNITED STATES PATENT AND TRADEMARK OFFICE
CERTIFICATE OF CORRECTION

PATENT NO. : 5,951,558
DATED : September 14,1999
INVENTOR(S) : Daniel FIZ

It is certified that error appears in the above-identified patent and that said Letters Patent is hereby corrected as shown below:

On the title page,[76]for inventor Daniel FIZ, add--Parana--before"754, 9th Floor"B", Buenos Aires, Argentina Signed and Sealed this Second Day of May, 2000

Attest:

Q. TODD DICKINSON

*Attesting Officer*  *Director of Patents and Trademarks*